US010062303B2

(12) United States Patent
Barnes et al.

(10) Patent No.: US 10,062,303 B2
(45) Date of Patent: *Aug. 28, 2018

(54) OBJECT TRACKING FOR ARTIFICIAL VISION

(71) Applicant: NATIONAL ICT AUSTRALIA LIMITED, Eveleigh, NSW (AU)

(72) Inventors: Nick Barnes, Eveleigh (AU); Chunhua Shen, Eveleigh (AU)

(73) Assignee: NATIONAL ICT AUSTRALIA LIMITED, Eveleigh, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/609,953

(22) Filed: May 31, 2017

(65) Prior Publication Data

US 2017/0263153 A1 Sep. 14, 2017

Related U.S. Application Data

(63) Continuation of application No. 13/498,667, filed as application No. PCT/AU2010/001290 on Sep. 30, 2010, now Pat. No. 9,697,746.

(30) Foreign Application Priority Data

Sep. 30, 2009 (AU) ................................ 2009904788

(51) Int. Cl.
*H04N 7/00* (2011.01)
*G06K 9/60* (2006.01)
(Continued)

(52) U.S. Cl.
CPC ........... *G09B 21/008* (2013.01); *G06K 9/605* (2013.01); *G06T 11/60* (2013.01); *A61F 9/08* (2013.01); *A61N 1/36046* (2013.01); *H04N 7/002* (2013.01)

(58) Field of Classification Search
CPC ...... A61F 9/08; A61N 1/36046; G06K 9/605; G06T 11/60; G09B 21/008; H04N 7/002
(Continued)

(56) References Cited

U.S. PATENT DOCUMENTS 5,777,715 A 7/1998 Kruegle et al.
5,802,294 A 9/1998 Ludwig et al.
(Continued)

FOREIGN PATENT DOCUMENTS

EP 0595556 10/1993
EP 1696396 8/2006
(Continued)

OTHER PUBLICATIONS

Extended European Search Report, EP Patent Application No. 10819750.0, dated Sep. 18, 2014, 12 pages.
(Continued)

*Primary Examiner* — Tung Vo
*Assistant Examiner* — Zaihan Jiang

(57) ABSTRACT

This invention concerns the tracking of objects in video data for artificial vision; for instance for a bionic eye. More particularly, the invention concerns a vision enhancement apparatus for a vision-impaired user. In other aspects, the invention concerns a method for enhancing vision and software to perform the method. The image processor operates to process video data representing images of a scene. Automatically detect and track a user selected object, such as a face, in the images. And, automatically modify the video data, by reserving a user selected area of the displayed images for displaying the tracked object as a separate video tile within the scene. The separate video tile remains in the selected area despite movement of the camera relative to the scene, or movement of the user relative to the object or the scene.

24 Claims, 1 Drawing Sheet

(51) Int. Cl.
*G09B 21/00* (2006.01)
*G06T 11/60* (2006.01)
*A61F 9/08* (2006.01)
*A61N 1/36* (2006.01)

(58) Field of Classification Search
USPC .................................. 348/143, 62, E07.085
See application file for complete search history.

(56) References Cited

U.S. PATENT DOCUMENTS

| | | | |
|---|---|---|---|
| 5,912,980 A | 6/1999 | Hunke | |
| 6,084,556 A * | 7/2000 | Zwern | G09B 21/008 345/158 |
| 6,307,526 B1 | 10/2001 | Mann | |
| 6,325,513 B1 | 12/2001 | Bergner et al. | |
| 6,516,247 B2 * | 2/2003 | Funada | G06K 9/00288 318/567 |
| 7,129,933 B1 * | 10/2006 | Nishikawa | G06F 3/03547 345/173 |
| 7,133,022 B2 | 11/2006 | Grabert | |
| 7,245,273 B2 * | 7/2007 | Eberl | G02B 27/017 345/7 |
| 7,272,306 B2 | 9/2007 | Zhang et al. | |
| 7,453,506 B2 * | 11/2008 | Li | H04N 5/23293 348/169 |
| 7,788,008 B2 | 8/2010 | Breed | |
| 7,990,422 B2 | 8/2011 | Ahiska et al. | |
| 9,697,746 B2 * | 7/2017 | Barnes | G09B 21/008 |
| 9,842,248 B2 * | 12/2017 | Greenberg | G06K 9/00288 |
| 2002/0008758 A1 | 1/2002 | Broemmelsiek et al. | |
| 2002/0113862 A1 | 8/2002 | Center, Jr. et al. | |
| 2003/0048928 A1 * | 3/2003 | Yavitz | G06F 17/27 382/114 |
| 2006/0056056 A1 | 3/2006 | Ahiska et al. | |
| 2006/0251382 A1 | 11/2006 | Vronay et al. | |
| 2007/0291104 A1 | 12/2007 | Petersen et al. | |
| 2008/0058894 A1 * | 3/2008 | Dewhurst | G09B 21/007 607/54 |
| 2008/0060034 A1 | 3/2008 | Egnal et al. | |
| 2008/0174659 A1 | 7/2008 | McDowall | |
| 2008/0316427 A1 | 12/2008 | Fisher et al. | |
| 2009/0055746 A1 * | 2/2009 | Dimitrova | G06F 17/30047 715/731 |
| 2010/0141662 A1 * | 6/2010 | Storey | G06T 13/40 345/473 |
| 2010/0220176 A1 | 9/2010 | Ziemeck et al. | |
| 2011/0285845 A1 | 11/2011 | Bedros et al. | |

FOREIGN PATENT DOCUMENTS

| | | |
|---|---|---|
| JP | 2005250772 | 9/2005 |
| JP | 2005277726 | 10/2005 |
| WO | WO 2006/106505 | 10/2006 |
| WO | WO 2009/078946 | 6/2009 |

OTHER PUBLICATIONS

Andrew Dankers et al., "MAP ZDF Segmentation and Tracking using Active Stereo Vision: Hand Tracking Case Study", Elsevier Science, Jun. 19, 2006, 26 pages.

Datong Chen et al., "Text detection and recognition in images and video frames", Pattern Recognition Society, published by Elsevier Ltd., 2003, 14 pages.

MR Everingham et al, "Head-mounted mobility aid for low vision using scene classification techniques", The International Journal of Virtual Reality, Aug. 31, 1999, 11 pages.

Examination report for corresponding EP Patent Application No. 10819750.0, dated Dec. 2, 2015, 8 pages.

International Search Report, PCT/AU2010/001290, completion date, Dec. 23, 2010 (5 pages).

Written Opinion of the International Search Report, PCT/AU2010/001290, completion date, Dec. 23, 2010 (7 pages).

* cited by examiner

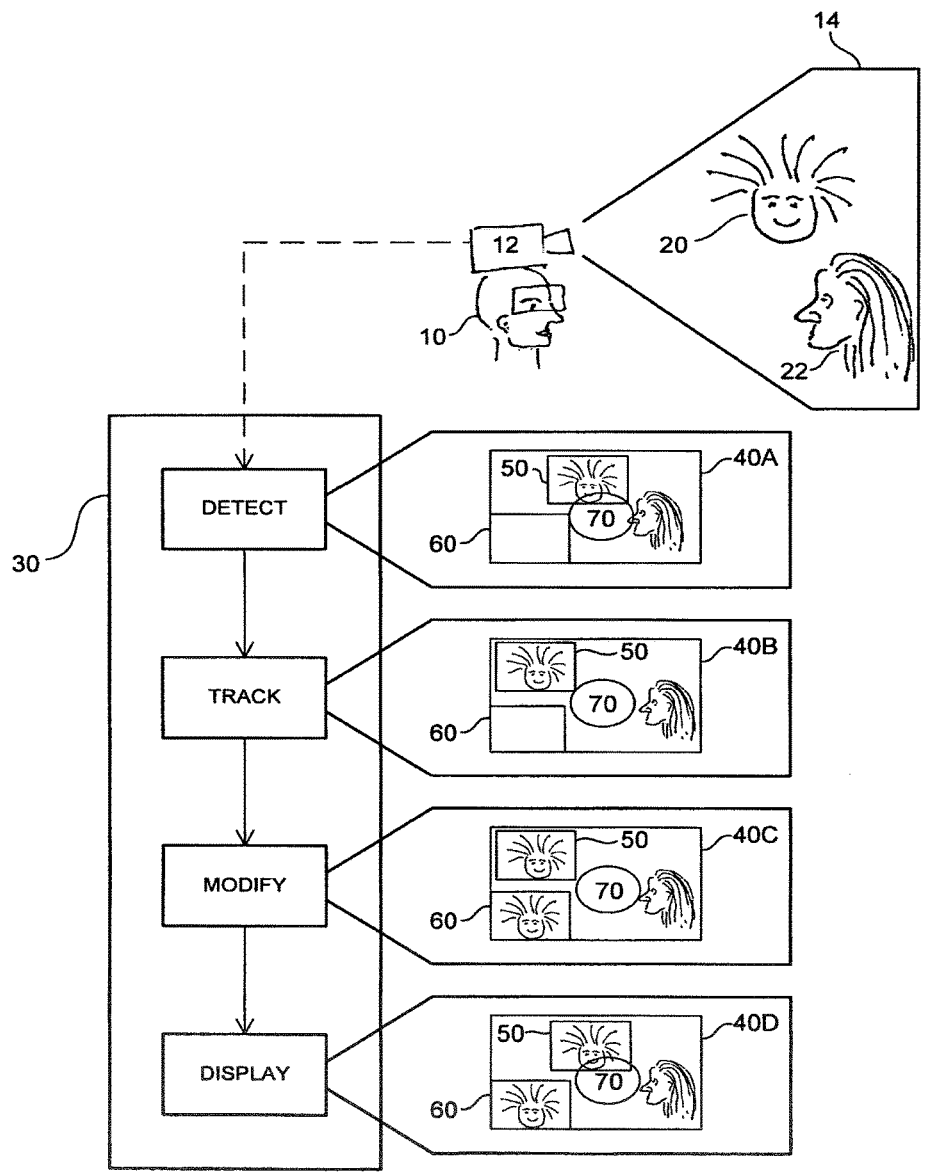

OBJECT TRACKING FOR ARTIFICIAL VISION

CROSS-REFERENCE TO RELATED APPLICATIONS

This application is a continuation of U.S. application Ser. No. 13/498,667, filed May 1, 2012 for "Object Tracking for Artificial Vision", which claims priority from PCT International Patent Application No. PCT/AU2010/001290, filed Sep. 30, 2010 and Australian Patent Application No. 2009904788, filed Sep. 30, 2009, which are hereby incorporated by reference herein.

TECHNICAL FIELD

This invention concerns the tracking of objects in video data for artificial vision; for instance for a bionic eye. More particularly, the invention concerns a vision enhancement apparatus for a vision-impaired user. In other aspects, the invention concerns a method for enhancing vision and software to perform the method.

BACKGROUND ART

Following the enormous success achieved by bionic ears in returning hearing to profoundly deaf people, interest has now turned to developing a bionic eye that will return sight to the blind.

The eye operates by focussing light onto the retina which in turn passes signals to the brain, via the optic nerve, where they are processed to provide sight. Partial or total blindness can be caused by damage or malfunction of any of the elements in the chain from eye to brain. However, many common forms of blindness results from damage to the retina, for instance macular degeneration leads to deterioration in the cells of the fovea, causing a blind spot in the centre of the field of vision; but leaving the peripheral vision intact. The idea behind the bionic eye is to artificially stimulate the retina using an electrode array implanted on top of it. Other visual aids, such as vision spectacles stimulate the retina using light but control the images presented before the user.

DISCLOSURE OF THE INVENTION

In a first aspect the invention is a vision enhancement apparatus for a vision-impaired user, comprising an image processor arranged to:
Process high resolution video data representing images of a scene.
Automatically detect and track a user selected object, such as a face, in the images.
Automatically modify the video data, by reserving a user selected area of the displayed images for displaying the tracked object as a separate video tile within the scene. The separate video tile remains in the selected area despite movement of the camera relative to the scene, or movement of the user relative to the object or the scene.

This invention allows important elements of the scene, such as the face of a friend, to be located in a part of the displayed image where it is visible to the vision-impaired user. For instance, if the user is suffering from macular degeneration the face may appear in their peripheral vision, where they can learn to see it. The face will remain in that part of the user's field of vision despite movement of the user or the object. The image of the face may also be maintained in a chosen orientation.

The user may have a high resolution video camera mounted on their head so that it films the scene in front of them. In the situation where the user is among a group of people they may turn their head in the direction of each other person as they speak. The object detection feature will detect faces in the images of the scene and may process the images to identify the person. The apparatus may announce the newly identified person to the user and then track their movements within the scene. While they remain in the scene their face may be continually tracked so the image of it is continually updated.

The apparatus may permit the user to select one or more objects to be displayed in respective reserved areas of the displayed images. This allows the user to select which people's faces are displayed in which part of their field of vision. It may alternatively allow the user to switch between the face detected faces, for instance when the user speaking to different people.

The face may be enlarged, or otherwise manipulated, to increase the user's perception of it, particularly of the facial expressions. Having high resolution images is very useful for subsequent image manipulation. An enlarged face or other object may be enlarged to highest resolution of the image. In general the apparatus may use default levels of enlargement for objects of different sizes, and this default may be overridden by user selection, for instance the user may override a face that has been presented to look at a single eye or move from one eye to the other.

The apparatus may provide the modified video data to a visual display, such as vision spectacles or a hand-held display, or to a retina, cortical or optic nerve implant that electrically stimulates nerves. It may also be able to provide video and still images off-line for later viewing by the user.

The entire apparatus could be worn by the user, either on the head as a cap, or distributed about the body.

In another aspect the invention is a method for enhancing vision, comprising the steps of:
Processing video data representing images of a scene.
Automatically detecting and tracking a user selected object in the images.
Automatically modifying the video data, by reserving a user selected area of the displayed images for displaying the tracked object in a separate video tile within the scene.

In a further aspect the invention is software to perform the method.

BRIEF DESCRIPTION OF THE DRAWINGS

An example of the invention will now be described with reference to the accompanying drawing, FIG. 1, which is a diagram that shows the system and explains the method of the invention.

BEST MODES OF THE INVENTION

The visually impaired user 10 wears an inconspicuous high resolution camera 12 and a pair of vision spectacles that provide a stereoscopic image of the scene 14 in front of the camera. Since the camera is worn by the user their movements cause the scene in front of the camera to change. In the scene shown there are two other people 20 and 22; friends of the user. As the three converse the user may move their head to face each of the friends 20 and 22 as they talk. Each of the three may also move around in the scene as they wish.

The camera 12 records the scene in front of it, and a processor 30 in the camera processes the recorded video data in real time. In FIG. 1 a single monoscopic image is shown being processed at four different instances of time, 40A, 40B, 40C and 40D.

The first thing the processor 30 does is to detect the face of user 20; at time 40A. Face detection algorithms work in different ways and this one uses a pre-trained model using statistical machine learning techniques and then draws a box 50 around the expected area of the face. The processor is able to track the face in the video data from frame to frame of the image despite movement of the face in the image; resulting from relative movement between the camera and the face.

The user 10 is able to choose which face, or faces, the processor will track depending upon how many faces the user is able to see. As one of the friends leave or another arrives the user is able to change their selection, for instance by pressing a button. Also, as people arrive at the scene, or leave, the processor may recognise that fact as the face is detected, and when detection ceases; these events can be announced to the user by means of an ear mounted speaker. The processor may consult a list of names associated with particular faces that have been previously recognised, and use this list to announce that a person has arrived or left.

The processor also modifies the video data by reserving an area 60 for the display of the chosen face. In this example the user suffers from macular degeneration and cannot see the central part of the image 70, but is able to see in their peripheral vision. As a result the processor in this case reserves the bottom left corner for the display of the chosen face in a separate video tile 60. The user is able to see this video tile, and therefore the face, in their peripheral vision.

The face may be digitally modified so that it appears frontal to the user, even if it is turned to one side; this may assist recognition.

This allows the user, for instance, to select the face of the friend they are talking with, and to see the changing expression on that face while they talk. When they start talking to someone else they can select the new face to be displayed in the separate video tile 60.

The processor may also enhance the user's vision of the face, for instance, by enlarging it or zooming in on part of it, such as the eyes. The enhancement is preserved as the face is tracked.

Although the invention has been described with reference to a particular example it should be appreciated that it could be practised in many other ways. For instance, instead of vision spectacles, the user may be fitted with a retina implant that electrically stimulates nerves. Also the entire apparatus could be worn by the user, either on the head as a cap, or distributed about the body.

It should also be understood that the user can interact with the system in any conceivable way, for instance pressing a button, using gestures such as pointing or head movements, or a mouth activated pressure sensor. In addition winking, blinking or eye tracking could be used, or any combination of these things.

For instance, head movements could be used to bring an object to a 'hotspot' such as the centre of the field of view where the object can be enlarged by blinking. Alternatively, eye movements could be used in concert with head movements. In another alternative the users hands may be recognised and used to point and gesture to select and enlarge objects.

Such interactions could also be used to control pan or tilt of the camera.

Depending on the users ability to see and the training they receive they may be able to perceive many different objects, or sets of objects, in reserved areas of the image. The objects themselves could be processed in many ways to make them more readily visible. As well as enlarging, the objects could for instance be coloured or distorted to increase the user's perception of them. This can be useful for hand to eye co-ordination, for instance to help the user manipulate door handles, cups, cutlery and the like. In this case the object may be enlarged while maintaining video tracking of it, so that the user has continuous video feedback as they manipulate it. Alternatively, the user may wish to enlarge their hands rather than the object. In this if the hand is touching or grasping something the computer may segment the object to facilitate the user interactively recognising it.

Other types of object may be enlarged but kept static, presenting the user with a still image. This could be useful for instance for instance to select an object from a set. Also, it is useful when an object is marked with writing, for instance a the packaging of products in a shop. This enables the user to read the label even when the object is no longer in front of the camera. The text may be rendered to the user in a typeface and size that makes it easier to read. Alternatively, image to voice software may also be used to read to read the label to the user. Similarly the text may be presented to the user via a braille tablet.

The apparatus may be operated by the user to switch back between these two modes of operation, so that after reading the label the user can find an item of the product and take it from the shelf. Moving on, the user may then read another label. There are many other situation where this functionality may be useful, for instance to identify the number of an approaching bus.

Machine learning may also be used to automate some of these sequences of commands. It could also be used to provide alerts to the user. For instance to detect the presence of particular people or objects itemised on a watch list. The alert may be given an any convenient way, for instance using sound, a tactile transducer or light. It may result in automatic actions such as enlarging the object.

When an object is lost from sight, for instance because a person has left the scene, an alert may be provided to the user. This could result in automatic zoom-out so that the remaining scene can be reviewed by the user.

A mode of operation may automatically provide information about the distance from the user to objects in the scene, for instance by providing a number associated with the object, colour-coding or by announcement to the user. Other types of information may also be provided. For instance, when a building is recognized the user may be informed of the location within the building they require and directions to it. If a bus is identified the user may be reminded about its route and frequency.

It should also be appreciated that the scene being viewed is not limited at all. It could be anything from a landscape to photographs or even movies.

The invention claimed is:
1. A vision enhancement apparatus for a vision-impaired user, comprising an image processor arranged to:
  process high resolution video data representing images of
    a scene and display the resulting images to the user;

automatically detect and track a user selected object in the images; and automatically modify the video data, by reserving a user selected area of the displayed images for displaying the tracked object as a separate video tile within the images of the scene to provide modified video data that includes:

the displayed images of the scene that includes the tracked object; and the separate video tile, at the user selected area within the displayed images, to display the tracked object, wherein the tracked object remains displayed at the separate video tile despite movement of the user or the tracked object.

2. A vision enhancement apparatus according to claim 1, wherein the object is identified within a first box and the separate video tile is a second box.

3. A vision enhancement apparatus according to claim 2, wherein the object in the first box is displayed in the separate video tile.

4. The vision enhancement apparatus according to claim 2, wherein the second box is the same size and shape as the first box.

5. A vision enhancement apparatus according to claim 1, wherein the user selects the location for the separate video tile such that it is located in a part of the displayed images where it is visible to the vision-impaired user.

6. A vision enhancement apparatus according to claim 5, wherein in the event the user is suffering from macular degeneration the separate video tile is located in their peripheral vision.

7. A vision enhancement apparatus according to claim 1, wherein the separate video tile will remain in that part of the user's field of vision despite movement of the user, the tracked object or a camera mounted on the head of the user for filming the scene in front of the user.

8. A vision enhancement apparatus according to claim 1, wherein the user has a high resolution video camera mounted on their head so that it films the scene in front of them.

9. A vision enhancement apparatus according to claim 1, wherein the processor automatically detects faces in the scene and processes the images to identify the faces.

10. A vision enhancement apparatus according to claim 9, wherein the apparatus announces newly identified faces to the user and then tracks their movements within the scene.

11. A vision enhancement apparatus according to claim 9, wherein while a face remains in the scene it is continually tracked so the image of it is continually updated to show its changing facial expressions in the separate video tile.

12. A vision enhancement apparatus according to claim 3, wherein the user is able to select more than one object to be displayed in respective separate video tiles of the displayed images.

13. A vision enhancement apparatus according to claim 12, wherein the user selects which objects are displayed and which video tile each is displayed in within the displayed images.

14. A vision enhancement apparatus according to claim 1, wherein the user is able to switch between the detected objects, to select the one which is displayed in the video tile.

15. A vision enhancement apparatus according to claim 1, wherein the object is enlarged, or otherwise manipulated, to increase the user's perception of it.

16. A vision enhancement apparatus according to claim 1, wherein the modified video data is, provided to a visual display, being vision spectacles, a retina, cortical or optic nerve implant.

17. A vision enhancement apparatus according to claim 1, wherein the user selected object is the users hands.

18. A vision enhancement apparatus according to claim 17, wherein the user selected object is in the users hands and the image processor operates to segment the object, to enable to user to interactively recognise it.

19. A vision enhancement apparatus according to claim 1, wherein the user selected object includes text or an object with text on it.

20. A vision enhancement apparatus according to claim 19, wherein the user is able to selectively switch between a still image of the text and a video image of the scene including the object.

21. A vision enhancement apparatus according to claim 1, wherein the apparatus automatically obtains and present information to the user about the selected object.

22. A vision enhancement apparatus according to claim 1, wherein the entire apparatus is distributed about a body of the user.

23. A method for enhancing vision, comprising the steps of:

processing high resolution video data representing images of a scene and displaying the resulting images to the user;

automatically detecting and tracking a user selected object in the images; and automatically modifying the video data, by reserving a user selected area of the displayed images for displaying the tracked object as a separate video tile within the images of the scene to provide modified video data that includes:

the displayed images of the scene that includes the tracked object; and the separate video tile, at the user selected area within the displayed images, to display the tracked object, wherein the tracked object remains displayed at the separate video tile despite movement of the user or the tracked object.

24. A non-transitory computer readable medium that provides instructions, which when executed by a processor, cause the processor to perform the processing steps of claim 23.

* * * * *